United States Patent [19]

Sakano et al.

[11] Patent Number: 4,511,574

[45] Date of Patent: Apr. 16, 1985

[54] N-(4-PHENYL-2-THIAZOLYL)CARBAMATE DERIVATIVES

[75] Inventors: Isao Sakano; Tatsuro Yokoyama; Seitaro Kajiya, all of Yokohama; Yutaka Okazaki; Hiroshi Tokuda, both of Mobara; Hiroshi Kawazura; Mikio Kumakura, both of Mobara; Takuo Nakano; Akira Awaya, both of Yokohama, all of Japan

[73] Assignee: Mitsui Toatsu Kagaku Kabushiki Kaisha, Tokyo, Japan

[21] Appl. No.: 417,115

[22] PCT Filed: Jan. 8, 1982

[86] PCT No.: PCT/JP82/00003
§ 371 Date: Sep. 8, 1982
§ 102(e) Date: Sep. 8, 1982

[87] PCT Pub. No.: WO82/02384
PCT Pub. Date: Jul. 22, 1982

[30] Foreign Application Priority Data

Jan. 8, 1981 [JP] Japan ............................. 56-714
May 18, 1981 [JP] Japan ........................... 56-73520

[51] Int. Cl.$^3$ .................. C07D 277/48; A01K 31/425
[52] U.S. Cl. .................................... 514/371; 548/196; 514/885
[58] Field of Search ......................... 548/196; 424/270

[56] References Cited

U.S. PATENT DOCUMENTS

| 4,027,031 | 5/1977 | DeBaun et al. .................. 514/371 |
| 4,217,355 | 8/1980 | Harbert et al. .................. 514/371 |
| 4,225,610 | 9/1980 | Tarayre et al. .................. 514/371 |

FOREIGN PATENT DOCUMENTS

| 44442 | 1/1982 | European Pat. Off. ............ 546/280 |
| 52-125164 | 2/1977 | Japan . |
| 54-154764 | 4/1979 | Japan . |
| 54-160369 | 6/1979 | Japan . |
| 54-61172 | 10/1979 | Japan . |

OTHER PUBLICATIONS

Metzger, Thiazole & its Derivatives, 232–235(1979).

Primary Examiner—Robert Gerstl
Attorney, Agent, or Firm—Birch, Stewart, Kolasch & Birch

[57] ABSTRACT

The present invention provides new chemical compounds, N-(4-phenyl-2-thiazolyl)carbamate derivatives, a process for preparing the same and pharmaceutical compositions containing the carbamate derivatives. More particularly, the present invention provides N-(4-phenyl-2-thiazolyl)carbamate derivatives which have immuno-modulating activity and are thus effective against immunodiseases such as chronic rheumatoid arthritis and also useful against viral diseases or for the immunotherapy of cancers with low toxicity.

9 Claims, No Drawings

N-(4-PHENYL-2-THIAZOLYL)CARBAMATE DERIVATIVES

BACKGROUND AND FIELD OF THE INVENTION

This invention relates to N-(4-phenyl-2-thiazolyl)carbamate derivatives, a process for preparing same and medicinal compositions containing same.

More particularly, this invention relates to N-(4-phenyl-2-thiazolyl)carbamate derivatives, which derivatives have immunomodulating activity and are thus effective against immunodiseases such as chronic rheumatoid arthritis and also useful against viral diseases or for the immunotherapy of cancers but display only a low toxicity, and are thus extremely desirous as medicines, a process for preparing same and medicinal compositions containing same.

A number of steroid-type and nonsteroid-type anti-inflammatory drugs have heretofore been clinically employed against autoimmune diseases such as rheumatism. However, these drugs are not quite satisfactory in their pharmacological effects, side effects and toxicity. The compounds of the present invention give a peculiar effect to cells participating in an immunity response so as to modulate the immunity response of the host. Although the disclosure of Japanese Laid-open Patent Appln. No. Sho. 54-61172 is known, which relates to compounds having a comparatively similar structure, the compounds of this invention have substituents different from those contained in such prior art compounds and possess important characteristics from a pharmacological standpoint.

DETAILED DESCRIPTION OF THE INVENTION

The present invention provides new chemical substances, i.e. N-(4-phenyl-2-thiazolyl)carbamates of the general formula (1):

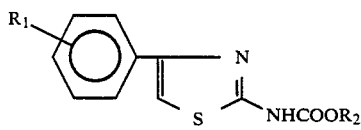
(1)

wherein $R_1$ denotes a lower alkylthio, lower alkylsulfinyl, lower alkylsulfonyl, nitro or amino group, and $R_2$ represents a lower alkyl or halogeno-lower alkyl group, a process for preparing these compounds and medical compositions containing the same.

In the above general formula, the term "lower alkyl group" means groups having 1–4 carbon atoms. As the compounds of the general formula (1) show tautomerism between their amine form and their imine form, the compounds of the general formula (1) in connection with the present invention embrace such tautomers.

Illustrative of the carbamate derivatives of the above general formula (1) concerned with the present invention wherein $R_2$ represents a lower alkyl group are, for example, lower alkyl esters of the following carbamic acids:

N-(4-p-methylthiophenyl-2-thiazolyl)carbamic acid;
N-(4-o-methylthiophenyl-2-thiazolyl)carbamic acid;
N-(4-m-methylthiophenyl-2-thiazolyl)carbamic acid;
N-(4-p-methylsulfinylphenyl-2-thiazolyl)carbamic acid;
N-(4-o-methylsulfinylphenyl-2-thiazolyl)carbamic acid;
N-(4-m-methylsulfinylphenyl-2-thiazolyl)carbamic acid;
N-(4-p-methylsulfonylphenyl-2-thiazolyl)carbamic acid;
N-(4-o-methylsulfonylphenyl-2-thiazolyl)carbamic acid;
N-(4-m-methylsulfonylphenyl-2-thiazolyl)carbamic acid;
N-(4-p-nitrophenyl-2-thiazolyl)carbamic acid;
N-(4-o-nitrophenyl-2-thiazolyl)carbamic acid;
N-(4-m-nitrophenyl-2-thiazolyl)carbamic acid;
N-(4-p-aminophenyl-2-thiazolyl)carbamic acid;
N-(4-o-aminophenyl-2-thiazolyl)carbamic acid; and
N-(4-m-aminophenyl-2-thiazolyl)carbamic acid.

On the other hand, examples wherein $R_2$ in the formula represents a halogeno-lower alkyl group include the following compounds:

2,2,2-trichloroethyl N-(4-p-methylthiophenyl-2-thiazolyl)carbamate;
2,2,2-trichloroethyl N-(4-o-methylthiophenyl-2-thiazolyl)carbamate;
2,2,2-trichloroethyl N-(4-m-methylthiophenyl-2-thiazolyl)carbamate;
2,2,2-trichloroethyl N-(4-p-methylsulfinylphenyl-2-thiazolyl)carbamate;
2,2,2-trichloroethyl N-(4-o-methylsulfinylphenyl-2-thiazolyl)carbamate;
2,2,2-trichloroethyl N-(4-p-methylsulfonylphenyl-2-thiazolyl)carbamate;
2,2,2-trichloroethyl N-(4-o-methylsulfonylphenyl-2-thiazolyl)carbamate;
2-chloroethyl N-(4-p-nitrophenyl-2-thiazolyl)carbamate;
2-chloroethyl N-(4-o-nitrophenyl-2-thiazolyl)carbamate;
2-chloroethyl N-(4-m-nitrophenyl-2-thiazolyl)carbamate;
2,2,2-trichloroethyl N-(4-p-nitrophenyl-2-thiazolyl)carbamate;
2,2,2-trichloroethyl N-(4-o-nitrophenyl-2-thiazolyl)carbamate;
2,2,2-trichloroethyl N-(4-m-nitrophenyl-2-thiazolyl)-carbamate;
2,2,2-trichloroethyl N-(4-p-aminophenyl-2-thiazolyl)-carbamate;
2,2,2-trichloroethyl N-(4-o-aminophenyl-2-thiazolyl)-carbamate; and
2,2,2-trichloroethyl N-(4-m-aminophenyl-2-thiazolyl)-carbamate.

These compounds represented by the general formula (1) are obtained by reacting 2-amino-4-phenylthiazoles represented by the general formula (2):

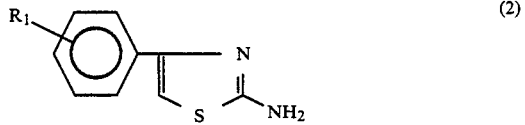
(2)

wherein $R_1$ has the same significance as defined in the general formula (1) with chloroformates having the general formaula (3):

XCOOR_2  (3)

wherein $R_2$ has the same significance as defined in the general formula (1) and X is a halogen atom.

The reaction may be carried out by either dissolving or suspending a starting material represented by the general formula (2)—which may optionally be in the form of a suitable acid addition salt—in a solvent and then adding dropwise or in a similar manner a compound of the general formula (3) to the solution or suspension. As suitable solvents used in this case are, for example, benzene toluene, xylene, acetone, ethyl methyl ketone, dioxane, 1,2-dimethoxyethane, tetrahydrofuran, and N,N-dimethylformamide. An organic base such as pyridine or triethylamine or an inorganic base such as sodium carbonate, potassium carbonate or sodium hydrogen carbonate can be used for the purpose of removing hydrogen halide formed in the course of the reaction.

The above reaction may proceed at temperatures below room temperature. However, it is possible to heat the reaction mixture up to the boiling point of the solvent in order to accelerate the reaction.

Most of the starting materials, namely, 2-amino-4-phenylthiazoles represented by the general formula (2) are known to the public and described in detail, for example, in a publication [Jacques V. Metzger, ed. "The Chemistry of Heterocyclic Compounds", Vol. 34; "Thiazole and Its Derivatives", Part Two, John Wiley & Sons (1979)].

Especially, regarding aminothiazoles containing a methylthiophenyl, methylsulfinylphenyl or methylsulfonylphenyl group, reference may be made to a technical paper [Chemia, 27, 99 (1973)].

As an alternative method for preparing the compounds represented by the general formula (1), α-halogenoacetophenones represented by the general formula (4):

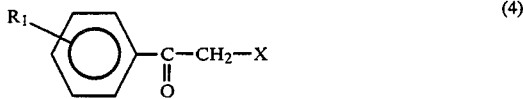

wherein $R_1$ denotes a lower alkylthio, lower alkylsulfinyl, lower alkylsulfonyl, nitro or amino group, and X stands for a halogen atom, are reacted with thioureas having the general formula (5):

wherein $R_2$ represents a lower alkyl or halogeno-lower alkyl group. The reaction is generally carried out by mixing these two compounds in a solvent such as an alcohol, tetrahydrofuran, dioxane, benzene, 1,2-dimethoxyethane or N,N-dimethylformamide. The reaction temperature may be selected at will, normally, from a temperature range between room temperature and the boiling point of the above solvent. The reaction is generally completed in 1–6 hours.

It is practical and advantageous, for the preparation of some of the derivatives represented by the general formula (1), especially N-(4-aminophenyl-2-thiazolyl)-carbamates, to subject the once-synthesized N-(4-nitrophenyl-2-thiazolyl)carbamates to reduction instead of following the above-described methods.

The compounds of this invention represented by the above general formula (1) have pharmacological activities. It has been unexpectedly found by the present inventors that the compounds according to this invention have immuno-modulating activity. Since the toxicity of these compounds is low, they are extremely useful as medicines.

This feature will hereinafter be described by way of test examples. Various test systems using animals have been routinely adopted for the determination of immunomodulating activity. Results of reinforcement tests of the delayed hypersensitivity, which are considered to be the most representative ones among such known test systems, will hereinafter be described by way of test example 1.

The delayed hypersensitivity induced on a mouse when picryl chloride(2-chloro-1,3,5-trinitrobenzene) is applied onto the skin of the mouse is known as a typical cellular immunity. This is one of the test systems commonly adopted throughout the world [see Asherson, G. L. and Ptak, W. "Contact and Delayed Hypersensitivity in the Mouse-I, Active Sensitization and Passive Transfer", Immunology, 15, 405–416 (1968)].

This test system was used for the reinforcement tests of the delayed hypersensitivity.

TEST EXAMPLE 1 (REINFORCEMENT TEST OF DELAYED HYPERSENSITIVITY)

Test Procedures:

Groups of eight ICR male mice, each having a body weight of about 30 g or so, were used for the test.

Sensitization was effected by applying a 3% solution of picryl chloride in a 4/1 mixture of olive oil and acetone onto the shaved abdomen of each of the mice.

Simultaneously with the sensitization, a solution or suspension of a compound according to this invention dissolved or suspended in a 0.2% solution of carboxymethyl cellulose in a physiological saline was orally administered to the mouse at a dose of 50 mg per Kg of its body weight. To each mouse of a control group, a 0.2% carboxymethylcellulose solution in a physiological saline was similarly administered.

The delayed hypersensitivity was induced 7 days after the sensitization by pinching each of the pinnae of each mouse with a pair of forceps whose tip portions were wrapped with a felt impregnated with a 1% solution of picryl chloride in olive oil and coating the pinnae with the solution. The thickness of each pinna was measured before the challenging and 24 hours after the challenging and the ratio of increase of the thickness (average value of both of the pinnae of the eight mice) is shown in Table 1.

For comparison, a similar test was carried out using Levamisole hydrochloride. These results are also shown therein.

F.t tests were carried out on the thus-obtained test results. Any group in which the test results were superior to those of the control group at significance levels of $P<0.05$ and $P<0.01$ are marked respectively, by an asterisk(*) and double asterisks(**).

Results: When a compound of the present invention was administered simultaneously with sensitization, the delayed hypersensitivity caused by a challenging was reinforced. The reinforcement effect of the compound according to this invention was recognized to be comparative to or higher than that attained by Levamisole which was used for the sake of comparison.

Thus, it is considered that the compounds of the present invention have an effect of modulating the cellular immunity response (immuno-modulating activity) in mice.

TABLE 1

Results of Reinforcement Tests of Delayed Hypersensitivity

| Compound | Ratio of Increase of Pinna Thickness (%) |
|---|---|
| NO$_2$—C$_6$H$_4$—CH=CH—S—C(=N)—NHCOOCH$_2$CCl$_3$ | 36.1* |
| CH$_3$SO$_2$—C$_6$H$_4$—CH=CH—S—C(=N)—NHCOOCH$_2$CCl$_3$ | 37.8* |
| NO$_2$—C$_6$H$_4$—CH=CH—S—C(=N)—NHCOOC$_2$H$_5$ | 34.8** |
| CH$_3$SO$_2$—C$_6$H$_4$—CH=CH—S—C(=N)—NHCOOC$_2$H$_5$ | 36.0** |
| Levamisole·HCl | 31.2* |

Next, a result of tests made on immuno-modulating activity in the adjuvant arthritis test is shown.

The adjuvant arthritis in rats caused by the injection of a Mycobacterium tuberculosis adjuvant is often utilized for a model test of chronic rheumatoid arthritis in the human.

The mechanism of manifestation of this disease has not completely been elucidated, but it is known that the cellular immunity plays an important role. The immuno-modulating activity of the compounds according to this invention was investigated in accordance with this known adjuvant arthritis test.

TEST EXAMPLE 2 (ADJUVANT ARTHRITIS TEST)(TABLE 2)

Test Procedures:

8-Week-old SD male rats were used for the test. In 0.1 ml of fluid paraffin, 0.4 mg of dry dead cells of *Mycobacterium tuberculosis* were suspended, and the suspension was injected under the heel skin of the right hind leg of each rat. Each of the compounds according to this invention was subcutaneously administered 9 times in total before and after the injection of the adjuvant. Each of the compounds of the present invention was dissolved or suspended in a 0.2% solution of carboxymethylcellulose in physiological saline and administered to each rat at a dose of 5 mg per Kg of the body weight. The swollen volume of the left hind leg was measured during the period extending from the day of injection to the day of completion of the test, and the swelling ratio was calculated. For comparison, a similar test was conducted using Levamisole hydrochloride. These results are also shown in Table 2. F.t tests were carried out on the test results obtained. Any group in which the test results were superior to those of a control group to which a 0.2% solution of carboxymethylcellulose in physiological saline was administered at significance levels of P<0.05, P<0.01 and P<0.001 are marked by an asterisk(*), double asterisks() and triple asterisks(*), respectively.

Results: The secondary inflammation of the adjuvant arthritis was remarkably suppressed by the compounds of the present invention. Their effects were statistically significant over the control group.

It was recognized that the compounds of the present invention exhibited an activity stronger than Levamisole used for comparison. Thus, they are considered to have immunomodulating activity and anti-arthritic activity.

TABLE 2

Results of Adjuvant Arthritis Test

| Compound | Number of cases | Swell supression ratio to control group (%) (average value from 16th to 20th days) |
|---|---|---|
| NO$_2$—C$_6$H$_4$—CH=CH—S—C(=N)—NHCOOCH$_2$CCl$_3$ | 10 | 45.0* |
| CH$_3$SO$_2$—C$_6$H$_4$—CH=CH—S—C(=N)—NHCOOCH$_2$CCl$_3$ | 10 | 30.0* |
| NO$_2$—C$_6$H$_4$—CH=CH—S—C(=N)—NHCOOC$_2$H$_5$ | 10 | 71.4*** |

TABLE 2-continued

Results of Adjuvant Arthritis Test

| Compound | Number of cases | Swell supression ratio to control group (%) (average value from 16th to 20th days) |
| --- | --- | --- |
| 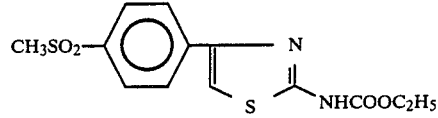 | 10 | 47.6** |
| Levamisole.HCl | 44 | 19.8** |

As illustrated in Test Examples 1 and 2, the compounds of the present invention have strong activity as immuno-modulating agents. Thus, they are effective for the remedy of diseases accompanied by abnormal change of an immune functions, for example, autoimmune diseases such as chronic rheumatoid arthritis. A toxicity test on the compounds of this invention will be shown in Test Example 3.

TEST EXAMPLE 3 (ACUTE TOXICITY TEST THROUGH ORAL ADMINISTRATION)

Test Procedures: To each of a group of five ddY male mice, was orally administered a medicine dissolved or suspended in physiological saline. They were watched for 7 days after the administration and an estimated $LD_{50}$ value was obtained.

Results: The estimated $LD_{50}$ value of the effective ingredient of a medicine according to this invention was 1,000 mg/Kg or higher. This value is far greater than the estimated $LD_{50}$ value of Levamisole·HCl, the latter value ranging 200-300 mg/Kg. Therefore, the toxicity of the effective ingredient of the present invention is considered to be low.

Although it is possible to use the compounds of this invention in the form of a free base as a raw material for preparing the medicaments, they may also be used in the form of a pharmaceutically acceptable salt as a raw material for preparing medicaments.

In case the compounds of this invention are used as medicaments, they may be administered in the same preparation form and according to the same administration method as in conventional immuno-modulating agents and carcinostatic agents. For instance, as preparations for oral administration they may be used in the form of capsules, granules, pills, fine grains, tablets or syrup. For administering through the rectum, suppositories are suitable. For injection, subcutaneous, intramuscular or intravenous injective preparations can be used.

As diseases to which the immuno-modulating agents of this invention can be applied, there may be mentioned diseases accompanied notably by an abnormal change of immune functions, for example, chronic rheumatoid arthritis; autoimmune diseases such as polymyositis; various infectious diseases; and a variety of cancers. It is expected that the immuno-modulating agents of this invention would normalize the immune functions of patients affected by such diseases.

It is desirous to choose a suitable administration method and an appropriate preparation form for the medicine of this invention depending on the type of disease and conditions of each patient. In case of oral administration, the dose of the compound is 0.5 to 100 mg, preferably 1 to 30 mg per Kg of the body weight per day. In case of administration to the rectum, the dose is suitably 1 to 100 mg per Kg of the body weight per day, while, in case of intravenous administration, the dose is preferably 1 to 10 mg per Kg of the body weight per day. Where it is administered subcutaneously or intra-muscularly, the dose of the compound of this invention is preferably 1 to 30 mg per Kg of the body weight per day. It is preferred that these doses be appropriately adjusted according to the type of diseases and the conditions of each patient. The therapeutic effect of the effective ingredient of the present invention may be increased, depending on the type of disease and the conditions of a patient, by using other medicines in combination. For example, when chemotherapeutic agents for cancers, such as alkylating agents and antimetabolics, which have a side effect of reducing the immunizing capacity of patients, are administered, the manifestation of such side effect may be prevented and their therapeutic effect may be synergistically increased if the compound of this invention is used in combination.

Examples of this invention will hereinafter be described.

EXAMPLE 1

Into 300 ml of acetone, were added 2.2 g of 2-amino-4-p-nitrophenylthiazole and 3.0 g of sodium hydrogen carbonate. To the resulting mixture, 6.3 g of 2,2,2-trichloroethyl chloroformate in 20 ml of acetone was added dropwise, followed by a stirring for 10 hours at the reflux temperature. Inorganic substances were filtered off and the filtrate was concentrated. Any substances, which were insoluble in diethyl ether, were removed from the concentrate. A crude reaction product resulting from the remaining portion, which was soluble in diethyl ether, was subjected to silica gel column chromatography. It was then eluted with a mixed solvent of chloroform-acetone (10:1) and thereafter recrystallized from chloroform to obtain 2.7 g of 2,2,2-trichloroethyl N-(4-p-nitrophenyl-2-thiazolyl)carbamate.

Melting point: 207°–209° C.

Elementary analysis values as $C_{12}H_8Cl_3N_3O_4S$:

|  | C | H | Cl | N | S |
| --- | --- | --- | --- | --- | --- |
| Calc. (%): | 36.34 | 2.03 | 26.82 | 10.59 | 8.08 |
| Found (%): | 36.26 | 2.07 | 27.05 | 10.75 | 8.13 |

IR, $\nu_{max}^{KBr}$ (cm$^{-1}$): 3370, 1740, 1600, 1550, 1510, 1340, 1220, 1110, 840, 725.

NMR, $\delta_{TMS}^{CDCl_3}$ (ppm): 5.17(2H, S), 8.17(1H, S), 8.35(2H, d), 8.45(2H, d), 12.76(1H, S: disappeared with D$_2$O).

EXAMPLE 2

Into tetrahydrofuran, were added 6.9 g of 2-amino-4-p-methylsulfinylphenylthiazole and 3.8 g of triethyl amine. The mixture was then cooled to −20°−−10° C., to which 7.4 g of 2,2,2-trichloroethyl chloroformate was added slowly. The reaction temperature was allowed to rise gradually to room temperature and the reaction mixture was stirred for 2 hours. Any insoluble substances were removed from the reaction mixture and the filtrate was subjected to silica gel column chromatography. The reaction product was eluted with a methylene/tetrachloride (20:1) mixed solvent, thereby obtaining 7.4 g of 2,2,2-trichloroethyl N-(4-p-methylsulfinyl-2-thiazolyl)carbamate.

Melting point: 242°–244° C.

Elementary analysis values as $C_{13}H_{11}Cl_3N_2O_2O_3S_2$:

|  | C | H | Cl | N | S |
|---|---|---|---|---|---|
| Calc. (%): | 37.74 | 2.68 | 25.71 | 6.77 | 15.50 |
| Found (%): | 37.67 | 2.59 | 25.61 | 6.77 | 15.27 |

NMR, $\delta_{TMS}^{DMSO-d6}$ (ppm): 2.8(3H, S), 5.08(2H, S), 7.6–8.3(5H, m), 12.5(1H, S: disappeared with D$_2$O).

EXAMPLE 3

In 50 ml of ethyl alcohol, 2.5 g of p-methylthiophenacyl bromide and 2.5 g of 2,2,2-trichloroethyl N-thiocarbamoylcarbamate were heated together with 1.1 g of triethylamine. They were reacted for 2 hours at the reflux temperature and, thereafter, ethyl alcohol was removed under reduced pressure. The residue was subjected to silica gel chromatography. The reaction product was eluted with a chloroform/methanol (20:1) mixed solvent to obtain 3.1 g of 2,2,2-trichloroethyl N-(4-p-methylthiophenyl-2-thiazolyl)carbamate.

Melting point: 164°–165° C.

Elementary analysis values as $C_{13}H_{11}Cl_3N_2O_2S_2$:

|  | C | H | Cl | N | S |
|---|---|---|---|---|---|
| Calc. (%): | 39.26 | 2.79 | 26.74 | 7.04 | 16.12 |
| Found (%): | 39.05 | 2.77 | 26.80 | 7.14 | 16.03 |

NMR, $\delta_{TMS}^{CDCl_3}$ (ppm): 2.45(3H, S), 4.63(2H, S), 7.0–7.9(5H, m), 10.8(1H, br: disappeared with D$_2$O).

The starting material, 2,2,2-trichloroethyl N-thiocarbamate, used in this Example is prepared as follows:

Into 75 ml of dry ethyl acetate, were added 7.3 g of anhydrous potassium thiocyanate and 15.7 g of 2,2,2-trichloroethyl chloroformate. The mixture was stirred at 60° C. for 1.5 hours. The reaction mixture was cooled in ice water, followed by an addition of an aqueous ammonia solution (29%) to render the reaction mixture alkaline. The solvent was removed under reduced pressure. The residue was treated with a water/methanol mixed solvent and the reaction product was obtained in a powdery form through filtration. It was then washed thoroughly with water to obtain 14.5 g of 2,2,2-trichloroethyl N-thiocarbamoylcarbamate.

Melting point: 177°–178.5° C.

Elementary analysis values are $C_4H_5Cl_3N_2O_2S$:

|  | C | H | Cl | N | S |
|---|---|---|---|---|---|
| Calc. (%): | 19.10 | 2.00 | 42.29 | 11.14 | 12.75 |
| Found (%): | 19.15 | 1.98 | 41.95 | 11.24 | 12.66 |

IR, $\nu_{max}^{KBr}$ (cm$^{-1}$): 3370, 3170, 1740, 1620, 1540, 1440, 1210, 1120, 1010, 865, 725.

NMR, $\delta_{TMS}^{MDSO-d6}$ (ppm): 4.95(2H, S), 8.9(1H, br: disappeared with D$_2$O), 9.4(1H, br: disappeared with D$_2$O), 11.35(1H, br: disappeared with D$_2$O).

EXAMPLE 4

Into 150 ml of ethyl acetate, was dissolved 3.9 g of the carbamate obtained in Example 1, followed by an addition of 3.5 g of 10% palladium/carbon. Into the resultant mixture, hydrogen was blown at normal pressure. When a stoichiometric amount of hydrogen was absorbed, the palladium catalyst was filtered off from the reaction mixture. The filtrate was concentrated and then subjected to silica gel column chromatography. The reaction product was eluted with a chloroform/ethyl acetate (10:1) mixed solvent. The resulting solid was recrystallized from ether to obtain 1.7 g of 2,2,2-trichloroethyl N-(4-p-aminophenyl-2-triazolyl)carbamate.

Melting point: 300° C. (decomposed).

Elementary analysis values as $C_{12}H_{10}Cl_3N_3O_2S$:

|  | C | H | Cl | N | S |
|---|---|---|---|---|---|
| Calc. (%): | 39.31 | 2.75 | 29.01 | 11.46 | 8.74 |
| Found (%): | 40.01 | 2.64 | 28.92 | 11.37 | 8.75 |

NMR, $\delta_{TMS}^{DMSO-d6}$ (ppm): 5.02(2H, S), 6.60(2H, d, J=8 Hz), 7.17(1H, S), 7.56(2H, d, J=8 Hz).

EXAMPLE 5

In accordance with the operations described in the foregoing Examples 1–3, the following compound was prepared:

2,2,2-Trichloroethyl N-(4-p-methylsulfonylphenyl-2-thiazolyl)carbamate

Melting point: 244°–246° C.

Elementary analysis values as $C_{13}H_{11}Cl_3N_2O_4S_2$:

|  | C | H | Cl | N | S |
|---|---|---|---|---|---|
| Calc. (%): | 36.33 | 2.58 | 24.75 | 6.52 | 14.92 |
| Found (%): | 36.35 | 2.68 | 24.87 | 6.58 | 15.05 |

NMR, $\delta_{TMS}^{DMSO-d6}$ (ppm): 3.2(3H, S), 5.06(2H, S), 7.8–8.4(5H, m), 12.5(1H, S: disappeared with D$_2$O).

EXAMPLE 6

The following compound was prepared in accordance with the operations described in Examples 1–3.

2,2,2-trichloroethyl-N-(4-m-nitrophenyl-2-thiazolyl)-carbamate

Melting point: 148°–149° C.

Elementary analysis values as $C_{12}H_8Cl_3N_3O_4S$:

|  | C | H | Cl | N | S |
|---|---|---|---|---|---|
| Calc. (%): | 36.34 | 2.03 | 26.82 | 10.59 | 8.08 |
| Found (%): | 36.52 | 1.98 | 26.80 | 10.50 | 7.88 |

NMR, $\delta_{TMS}^{CDCl_3}$ (ppm): 4.80(2H, s), 7.36(1H, s), 7.5–8.7(4H, m), 9.97(1H, s: disappeared with D$_2$O).

EXAMPLE 7

In 300 ml of tetrahydrofuran, was suspended 4.42 g of 2-amino-4-p-nitrophenylthiazole, followed by a further addition of 20 ml of triethylamine. The mixture was cooled to about 5° C., to which 10.5 ml of ethyl chloroformate was added dropwise. Then, the reaction mixture was stirred at room temperature for 3.5 days. Any insoluble matter was filtered off from the reaction mixture, and the filtrate was concentrated and then washed in ethyl acetate successively with water, dilute hydrochloric acid, and water. Then, the ethyl acetate solution was concentrated to about 50 ml and the resulting crystals were separated by filtration and then subjected to column chromatography on silica gel. The reaction product was eluted with a benzene/ethyl acetate mixed solvent. The resultant product was recrystallized from ethyl acetate to obtain 2.8 g of ethyl N-(4-p-nitrophenyl-2-thiazolyl)carbamate.

Melting point: 224°–226° C.

Elementary analysis values for $C_{12}H_{11}N_3O_4S$:

|  | C | H | N | S |
|---|---|---|---|---|
| Calc. (%): | 49.14 | 3.78 | 14.33 | 10.93 |
| Found (%): | 49.09 | 3.79 | 14.37 | 10.87 |

NMR, $\delta_{TMS}^{DMSO-d6}$ (ppm): 1.34(3H, t: J=7 Hz), 4.26(2H, q: J=7 Hz), 7.88(1H, s), 8.08(2H, d: J=8 Hz), 8.26 (2H, d: J=8 Hz), 11.88(1H, s).

EXAMPLE 8

In 50 ml of tetrahydrofuran, was dissolved 2.22 g of 2-amino-4-p-methylthiophenylthiazole, followed by a further addition of 3.6 g of triethylamine. The mixture was cooled to about 5° C., to which 3.3 g of ethyl chloroformate was added dropwise. Then, the mixture was stirred at room temperature for 3 hours. The resultant reaction mixture was concentrated and 150 ml of methanol was added to the concentrate. The mixture was warmed to 45° C. Any insoluble matter was removed. The methanol-soluble portion was concentrated and the residue was subjected to silica gel chromatography. The reaction product was eluted with a chloroform/tetrahydrofuran mixed solvent. It was then recrystallized from methanol to obtain 1.2 g of methyl N-(4-p-methylthiophenyl-2-thiazolyl)carbamate.

Melting point: 193.5°–195° C.

Elementary analysis values for $C_{12}H_{12}N_2O_2S_2$:

|  | C | H | N | S |
|---|---|---|---|---|
| Calc. (%): | 51.41 | 4.31 | 9.99 | 22.87 |
| Found (%): | 51.54 | 4.24 | 9.91 | 23.08 |

NMR, $\delta_{TMS}^{DMSO-d6}$ (ppm): 2.52(3H, s), 3.78(3H, s), 7.46(1H, s), 7.2–7.84(4H, m), 11.8(1H, s).

Compounds of the following Examples 9–14 were synthesized in accordance with the operations described in Example 7 or 8:

EXAMPLE 9

Ethyl N-(4-p-methylsulfinylphenyl-2-thiazolyl)carbamate

Melting point: 209°–211° C. (decomposed).

Elementary analysis values as $C_{13}H_{14}N_2O_3S_2$:

|  | C | H | N | S |
|---|---|---|---|---|
| Calc. (%): | 50.30 | 4.55 | 9.03 | 20.66 |
| Found (%): | 50.11 | 4.56 | 8.96 | 20.61 |

NMR, $\delta_{TMS}^{DMSO-d6}$ (ppm): 1.28(3H, t: J=7.5 Hz), 2.80(3H, s), 4.24(2H, q: J=7.5 Hz), 7.74(1H, s), 7.66–8.12(4H, m), 11.88(1H, s).

EXAMPLE 10 n-Butyl N-(4-p-methylsulfinylphenyl-2-thiazolyl)carbamate

Melting point: 178°–179° C.

Elementary analysis values as $C_{15}H_{18}N_2O_3S_2$:

|  | C | H | N | S |
|---|---|---|---|---|
| Calc. (%): | 53.23 | 5.36 | 8.28 | 18.95 |
| Found (%): | 53.22 | 5.44 | 8.19 | 18.84 |

NMR, $\delta_{TMS}^{DMSO-d6}$ (ppm): 0.96(3H, t: J=7.5 Hz), 1.22–1.84(4H, m), 2.84(3H, s), 4.24(2H, t: J=7.5 Hz), 7.8(1H, s), 7.72–8.20(4H, m), 11.92(1H, s).

EXAMPLE 11

Ethyl N-(4-p-methylsulfonylphenyl-2-thiazolyl)carbamate

Melting point: 248°–250° C.

Elementary analysis values as $C_{13}H_{14}N_2O_4S_2$:

|  | C | H | N | S |
|---|---|---|---|---|
| Calc. (%): | 47.84 | 4.32 | 8.58 | 19.65 |
| Found (%): | 47.70 | 4.41 | 8.40 | 19.49 |

NMR, $\delta_{TMS}^{DMSO-d6}$ (ppm): 1.28(3H, t: J=7.5 Hz), 3.24 (3H, s), 4.23(2H, q: J=7.5 Hz), 7.84(1H, s), 7.90–8.18(4H, m), 11.92(1H, s).

EXAMPLE 12 n-Butyl N-(4-p-methylsulfonylphenyl-2-thiazolyl)carbamate

Melting point: 191°–192° C.

Elementary analysis values as $C_{15}H_{18}N_2O_4S_2$:

|  | C | H | N | S |
|---|---|---|---|---|
| Calc. (%): | 50.83 | 5.12 | 7.90 | 18.09 |
| Found (%): | 50.62 | 5.20 | 7.85 | 17.98 |

NMR, $\delta_{TMS}^{DMSO-d6}$ (ppm): 0.95(3H, t: J=7.5 Hz), 1.20–1.84(4H, m), 3.18(3H, s), 4.23(2H, t: J=7.5 Hz), 7.90(1H, s), 7.92–8.26(4H, m), 12.00(1H, s).

EXAMPLE 13

Methyl N-(4-p-nitrophenyl-2-thiazolyl)carbamate

Melting point: 252°–254° C.

Elementary analysis values as $C_{12}H_{11}N_3O_4S$:

|  | C | H | N | S |
|---|---|---|---|---|
| Calc. (%): | 49.14 | 3.78 | 14.33 | 10.93 |
| Found (%): | 49.05 | 3.67 | 14.33 | 11.02 |

EXAMPLE 14 n-Butyl N-(4-p-nitrophenyl-2-thiazolyl)carbamate

Melting point: 141°–144° C.

Elementary analysis values as $C_{14}H_{15}N_3O_4S$:

|  | C | H | N | S |
| --- | --- | --- | --- | --- |
| Calc. (%): | 52.33 | 4.70 | 13.08 | 9.98 |
| Found (%): | 52.43 | 4.81 | 13.01 | 10.00 |

NMR, $\delta_{TMS}^{CDCl_3}$ (ppm): 0.86(3H, t), 1.00–1.95(4H, m), 4.01–4.18 (2H, m), 7.26(1H, s), 7.80–8.28(4H, m), 9.70(1H, s).

EXAMPLE 15

In 500 ml of ethyl acetate, was dissolved 4 g of ethyl N-(4-p-nitrophenyl-2-thiazolyl)carbamate, followed by an addition of 3 g of a 10% palladium/carbon catalyst. The mixture was then subjected under normal pressure to reduction with hydrogen gas. The catalyst was filtered off. The filtrate was concentrated and subjected to column chromatography on silica gel. The reaction product was eluted with a chloroform/ethylacetate mixed solvent. The resulting product was then recrystallized from methanol to obtain 2.6 g of ethyl N-(4-p-aminophenyl-2-thiazolyl)carbamate.

Melting point: 300° C. or higher.

Elementary analysis values as $C_{12}H_{13}N_3O_2S$:

|  | C | H | N | S |
| --- | --- | --- | --- | --- |
| Calc. (%): | 54.74 | 4.98 | 15.96 | 12.18 |
| Found (%): | 54.66 | 5.13 | 15.95 | 12.00 |

NMR, $\delta_{TMS}^{DMSO-d_6}$ (ppm): 1.29(3H, t: J=7 Hz), 4.22(2H, q: J=7 Hz), 7.12(1H, s), 6.58(2H, d: J=8 Hz), 7.54 (2H, d: J=8 Hz).

We claim:

1. An N-(4-phenyl-2-thiazolyl)carbamate compound represented by the formula:

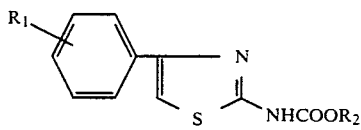

wherein $R_1$ denotes a lower alkylsulfinyl, lower alkylsulfonyl, nitro or amino group, and $R_2$ represents a lower alkyl or halogeno-lower alkyl group.

2. A compound as claimed in claim 1, wherein $R_1$ is methylsulfinyl, methylsulfonyl, nitro or amino.

3. A compound as claimed in claim 2, wherein $R_2$ is 2,2,2-trichloroethyl or a lower alkyl group having 1–4 carbon atoms.

4. A pharmaceutical composition having immunomodulating activity comprising an effective immunomodulating amount of a compound according to claim 1 or a pharmaceutically acceptable salt thereof, and a pharmaceutically acceptable carrier or diluent.

5. A pharmaceutical composition having immunomodulating activity comprising an effective immunomodulating amount of a compound according to claim 2 or a pharmaceutically acceptable salt thereof, and a pharmaceutically acceptable carrier or diluent.

6. A pharmaceutical composition having immunomodulating activity comprising an effective immunomodulating amount of a compound according to claim 3 or a pharmaceutically acceptable salt thereof, and a pharmaceutically acceptable carrier or diluent.

7. A method for the treatment of a patient suffering from an abnormality in immune function which comprises administering to said patient an effective immunomodulating amount of a compound according to claim 1.

8. A method for the treatment of a patient suffering from an abnormality in immune function which comprises administering to said patient an effective immunomodulating amount of a compound according to claim 2.

9. A method for the treatment of a patient suffering from an abnormality in immune function which comprises administering to said patient an effective immunomodulating amount of a compound according to claim 3.

* * * * *